United States Patent
Venkataramani et al.

(10) Patent No.: US 12,059,296 B2
(45) Date of Patent: Aug. 13, 2024

(54) SYSTEMS AND METHODS FOR GENERATING ULTRASOUND PROBE GUIDANCE INSTRUCTIONS

(71) Applicant: GE Precision Healthcare LLC, Wauwatosa, WI (US)

(72) Inventors: Rahul Venkataramani, Bangalore (IN); Vikram Melapudi, Bangalore (IN); Pavan Annangi, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 176 days.

(21) Appl. No.: 17/143,586

(22) Filed: Jan. 7, 2021

(65) Prior Publication Data

US 2022/0061803 A1  Mar. 3, 2022

(30) Foreign Application Priority Data

Aug. 26, 2020  (IN) .............................. 202041036670

(51) Int. Cl.
*A61B 8/00* (2006.01)
*A61B 8/08* (2006.01)
*A61B 34/20* (2016.01)

(52) U.S. Cl.
CPC ............ *A61B 8/4263* (2013.01); *A61B 8/466* (2013.01); *A61B 8/483* (2013.01); *A61B 8/488* (2013.01); *A61B 34/20* (2016.02); *A61B 2034/2063* (2016.02)

(58) Field of Classification Search
CPC ....... A61B 8/4263; A61B 8/466; A61B 8/483; A61B 8/488; A61B 34/20; A61B 2034/2063; A61B 8/54; A61B 8/5207; A61B 8/5253; G06N 20/00
See application file for complete search history.

(56) References Cited

U.S. PATENT DOCUMENTS

| | | | |
|---|---|---|---|
| 2009/0046912 A1* | 2/2009 | Hostettler | G06T 5/50 382/131 |
| 2011/0170752 A1* | 7/2011 | Martin | A61B 8/58 382/128 |
| 2013/0150719 A1* | 6/2013 | Orderud | G06T 19/00 600/443 |

(Continued)

OTHER PUBLICATIONS

Burke et al. "Learning robotic ultrasound scanning using probabilistic temporal ranking," arXiv preprint arXiv:2002.01240 (2020), 11 pages.

(Continued)

*Primary Examiner* — Alexei Bykhovski (57) ABSTRACT

Systems, machine-readable media, and methods for ultrasound imaging can include acquiring three-dimensional data for one or more patient data sets and generating a three-dimensional environment based on one or more transition areas identified between a plurality of volumes of the three-dimensional data. A method can also include generating a set of probe guidance instructions based at least in part on the one or more transition areas and the plurality of volumes of the three-dimensional data, and acquiring, using an ultrasound probe, a first frame of two-dimensional data for a patient. The method can also include executing the set of probe guidance instructions to provide probe feedback for acquiring at least a second frame of two-dimensional data.

17 Claims, 4 Drawing Sheets

(56) References Cited

U.S. PATENT DOCUMENTS

| | | | |
|---|---|---|---|
| 2014/0267267 A1* | 9/2014 | Piper | G06T 3/4038 |
| | | | 345/424 |
| 2017/0311923 A1* | 11/2017 | Saberi | A61B 8/4488 |
| 2020/0097811 A1* | 3/2020 | Ma | G06N 20/00 |
| 2020/0229798 A1* | 7/2020 | Leyvi | G16H 40/63 |
| 2020/0289096 A1* | 9/2020 | Aase | A61B 8/4488 |
| 2021/0035340 A1* | 2/2021 | Wang | G06V 10/82 |
| 2022/0015741 A1* | 1/2022 | Amador Carrascal | A61B 8/42 |

OTHER PUBLICATIONS

Dou et al, "Agent with Warm Start and Active Termination for Plane Localization in 3D Ultrasound," International Conference on Medical Image Computing and Computer-Assisted Intervention. Springer, Cham, 2019, 9 pages.

Li et al. "Standard plane detection in 3d fetal ultrasound using an iterative transformation network," International Conference on Medical Image Computing and Computer-Assisted Intervention. Springer, Cham, 2018, 9 pages.

Milletari et al., "Straight to the point: reinforcement learning for user guidance in ultrasound," Smart Ultrasound Imaging and Perinatal, Preterm and Pediatric Image Analysis. Springer, Cham, 2019. 3-10, 11 pages.

\* cited by examiner

SYSTEMS AND METHODS FOR GENERATING ULTRASOUND PROBE GUIDANCE INSTRUCTIONS

CROSS-REFERENCE TO RELATED APPLICATIONS

The present application claims the benefit of Indian Patent Application No. 202041036670, filed on Aug. 26, 2020 and titled "SYSTEMS AND METHODS FOR GENERATING ULTRASOUND PROBE GUIDANCE INSTRUCTIONS," the contents of which are incorporated herein by reference in their entirety.

TECHNICAL FIELD

This disclosure relates generally to methods and ultrasound imaging systems for generating three-dimensional environments used for training artificial intelligence tools to provide ultrasound probe guidance instructions.

BACKGROUND

Ultrasound imaging systems are used to acquire data that may create an image of internal body structures such as blood vessels, tendons, joints, muscles, and organs, among others. The ultrasound imaging systems can send sound wave pulses with any suitable frequencies into tissue of a patient and the sound wave pulses echo off the tissue of the patient with different reflective properties. The reflection of the sound wave pulses can be detected and analyzed to produce an image of internal body structures.

As sound wave pulse data is acquired or obtained with an ultrasound imaging system, artifacts may be present that obscure or obfuscate regions of internal body structures. The ultrasound probe of the ultrasound imaging system can be reoriented, tilted, or otherwise moved in a different direction to acquire a clear image of internal body structures with minimal artifacts or any other objects that may obscure an internal body structure. Techniques for providing instructions to an ultrasound probe can enable acquiring imaging data without artifacts or obscured regions.

SUMMARY

This summary introduces concepts that are described in more detail in the detailed description. It should not be used to identify essential features of the claimed subject matter, nor to limit the scope of the claimed subject matter.

In an aspect, a method for ultrasound imaging includes acquiring three-dimensional data for one or more patient data sets and generating a three-dimensional environment based on one or more transition areas identified between a plurality of volumes of the three-dimensional data. The method can also include generating a set of probe guidance instructions based at least in part on the three-dimensional environment, acquiring, using an ultrasound probe, a first frame of two-dimensional data for a patient, and executing the set of probe guidance instructions to provide probe feedback for acquiring at least a second frame of two-dimensional data for the patient.

In some examples, the probe feedback can include a recommended ultrasound probe path for the ultrasound probe. In some aspects, the generating the set of probe guidance can include determining a cost function using a machine learning technique based at least on one or more simulated frames acquired from the three-dimensional environment. In some examples, the ultrasound probe comprises a three-dimensional ultrasound probe or a two-dimensional ultrasound probe.

In some aspects, at least one three-dimensional ultrasound probe acquires the three-dimensional data for the one or more patient data sets, and the ultrasound probe that acquires the first frame is a two-dimensional ultrasound probe that acquires the two-dimensional data that is used to execute the set of probe guidance instructions. In some examples, the method can include acquiring a simulated frame from the three-dimensional environment. In some aspects, the method can include imposing a scan cone mask to the simulated frame to represent output from the ultrasound probe. In some examples, the method can include augmenting the simulated frame based on non-geometric configuration settings of the ultrasound probe. In some aspects, the recommended ultrasound probe path of the ultrasound probe can include a direction of the ultrasound probe, a subsequent scan angle of the ultrasound probe, or a combination thereof.

In some examples, each volume of the three-dimensional data can include Doppler data from one or more regions of a patient, B-mode data from the one or more regions of the patient, or a combination thereof. In some aspects, the method can include displaying the recommended ultrasound probe path using a display device electronically coupled to the ultrasound probe. In some examples, the method can include displaying, using a user interface, a real-time image and displaying the recommended ultrasound probe path with the user interface.

In an aspect, an ultrasound imaging system can include a display device to provide a user interface, an ultrasound probe, and a processor to acquire three-dimensional data for one or more patient data sets. The processor can also generate a three-dimensional environment based on one or more transition areas identified between a plurality of volumes of the three-dimensional data, generate a set of probe guidance instructions based at least in part on the one or more transition areas and the plurality of volumes of the three-dimensional data, and acquire, using an ultrasound probe, a first frame of two-dimensional data for a patient. The processor can also execute the set of probe guidance instructions to provide probe feedback for controlling the ultrasound probe to acquire at least a second frame of two-dimensional data, and display the probe feedback using the display device.

In another aspect, a non-transitory machine-readable medium for ultrasound imaging can include a plurality of instructions that, in response to execution by a processor, cause the processor to acquire three-dimensional data for one or more patient data sets. The instructions can also cause the processor to generate a three-dimensional environment based on one or more transition areas identified between a plurality of volumes of the three-dimensional data, generate a set of probe guidance instructions based at least in part on the one or more transition areas and the plurality of volumes of the three-dimensional data, and acquire, using an ultrasound probe, a first frame of two-dimensional data for a patient. In some examples, the instructions can cause the processor to execute the set of probe guidance instructions to provide probe feedback for controlling the ultrasound probe to acquire at least a second frame of two-dimensional data, and display the probe feedback using the display device, wherein the probe feedback comprises a recommended ultrasound probe path of the ultrasound probe comprising a direction of the ultrasound probe, a subsequent scan angle of the ultrasound probe, or a combination thereof.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present techniques will be better understood from reading the following description of non-limiting examples, with reference to the attached drawings, wherein below.

DETAILED DESCRIPTION

Figure 4:
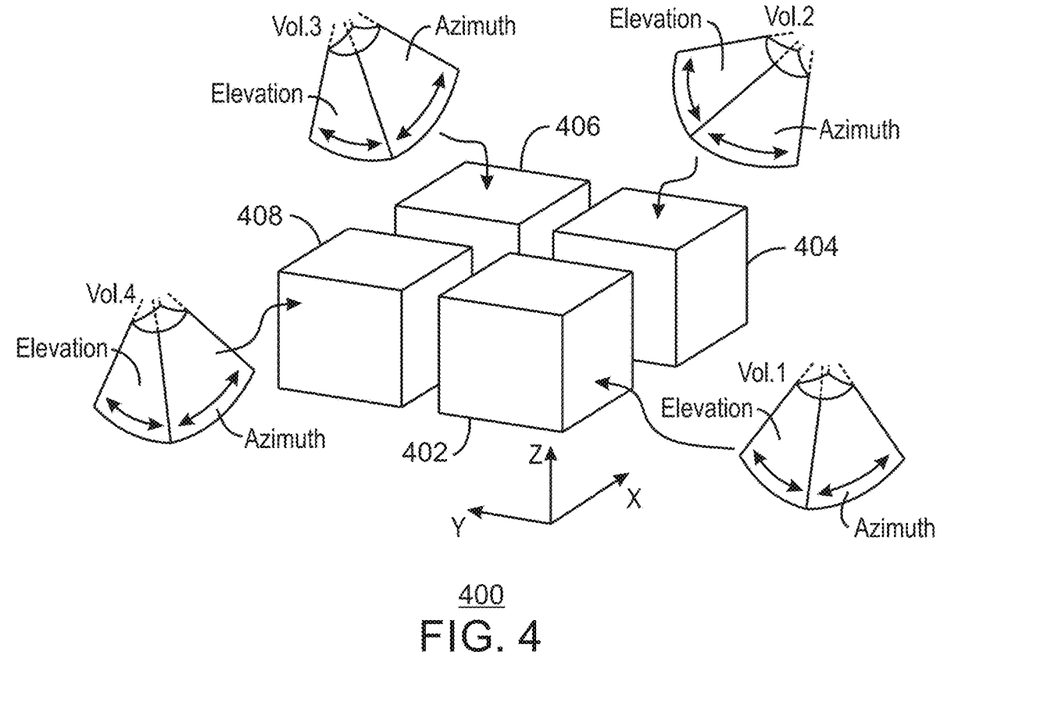
FIG. 4 is a schematic representation of example volumes of a three-dimensional environment according to an example.
Figure 5:
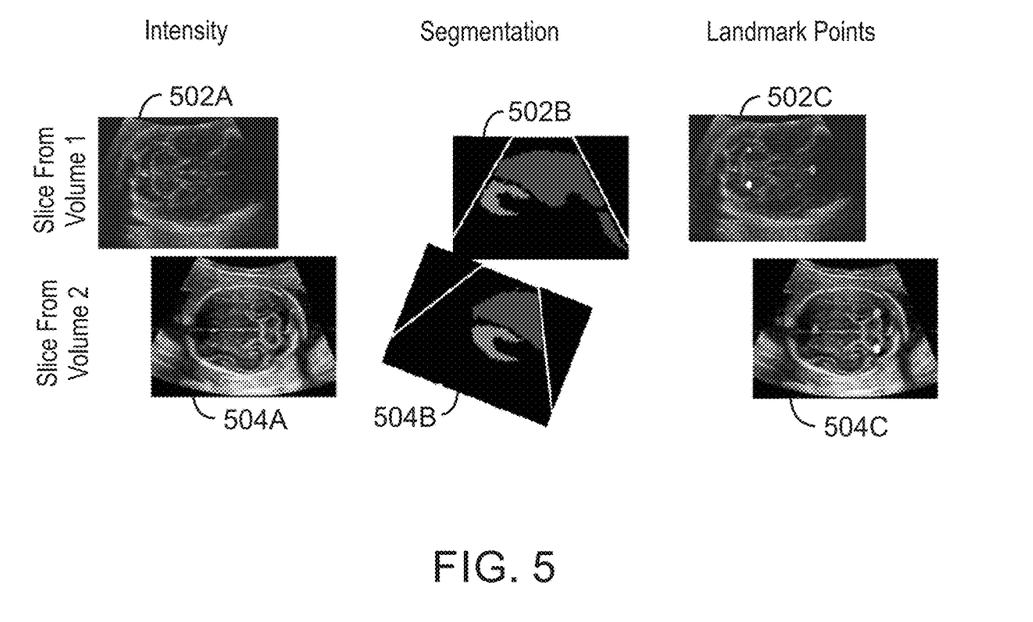
FIG. 5 shows example techniques for generating a three-dimensional environment with volumes according to an example.
Figure 6:
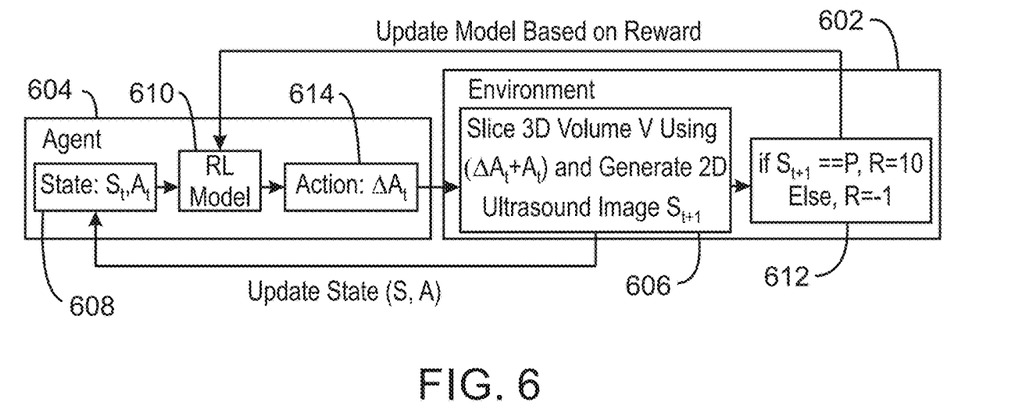
FIG. 6 is a process flow diagram of an example method for generating probe guidance instructions with a reinforcement learning technique according to an example.
Figure 7:
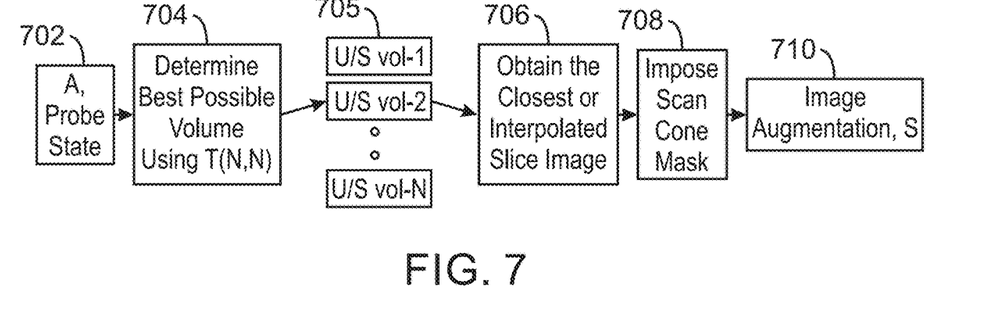
FIG. 7 is a process flow diagram of an example method for generating probe guidance instructions using a three-dimensional environment according to an example.
Figure 8:
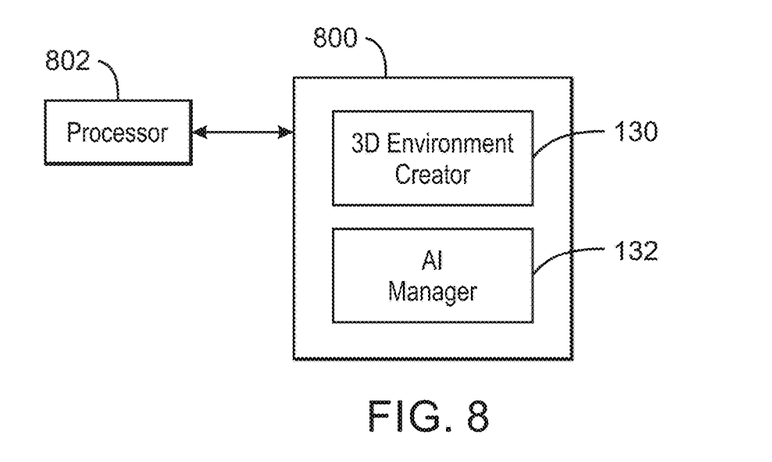
FIG. 8 is block diagram of a non-transitory machine-readable medium for generating probe guidance instructions based on a three-dimensional environment according to an example.

Embodiments of the present disclosure will now be described, by way of example, with reference to FIGS. 1-8, in which the following description relates to various examples of medical imaging systems such as ultrasound probes. In particular, systems and methods are provided for generating a three-dimensional environment based on data from ultrasound probes and generating artificial intelligence instructions to provide guidance for the use of ultrasound probes based on the three-dimensional environment. The artificial intelligence instructions can be generated, trained, or otherwise initiated to provide guidance for use of an ultrasound probe to avoid artifacts and to acquire data along a preferred path for guiding the ultrasound probe along an expected anatomical scan plane. An artifact, as referred to herein, can include any metallic object, non-metallic object, unrequested organ, or the like, that obscures or obfuscates a medical image. An example of a medical imaging system, such as an ultrasound probe, that can obtain data to generate the three-dimensional environment and to execute artificial intelligence instructions in accordance with the present techniques is provided in FIGS. 1 and 2. One approach to generating the artificial intelligence instructions, such as the method depicted in FIG. 3, can include generating a three-dimensional environment based on ultrasound data and using a reinforcement learning technique, among others, to identify a recommended path for an ultrasound probe to use when acquiring ultrasound data for one or more organs of a patient. FIGS. 4 and 5 illustrate examples techniques for generating a three-dimensional environment with volumes of ultrasound data. FIGS. 6 and 7 illustrate example techniques for generating probe guidance instructions to provide guidance for using an ultrasound probe based at least in part on the generated three-dimensional environment. FIG. 8 provides an example non-transitory, machine-readable media for generating the three-dimensional environment and the probe guidance instructions.

The technical effect of generating probe guidance instructions, with artificial intelligence instructions, to provide guidance for an ultrasound probe can prevent acquiring artifacts in a scan range of an area of interest of a patient and can prevent the acquisition of obscured, blurry, or obfuscated areas. Accordingly, the present techniques have a technical advantage of reducing a time period to acquire a scan of a patient with an ultrasound probe by ensuring that the ultrasound probe data does not include artifacts. The present techniques can also reduce the data storage and processing time of an ultrasound probe by providing a recommended path for an ultrasound probe during a scan. This can reduce the amount of acquired ultrasound data from an unexpected or undesirable angle, orientation, or the like.

In the following detailed description, reference is made to the accompanying drawings that form a part hereof, and in which is shown by way of illustration specific examples that may be practiced. These examples are described in sufficient detail to enable those skilled in the art to practice the examples, and it is to be understood that other examples may be utilized and that logical, mechanical, electrical and other changes may be made without departing from the scope of the examples. The following detailed description is, therefore, not to be taken as limiting the scope of the examples herein.

Figure 1:
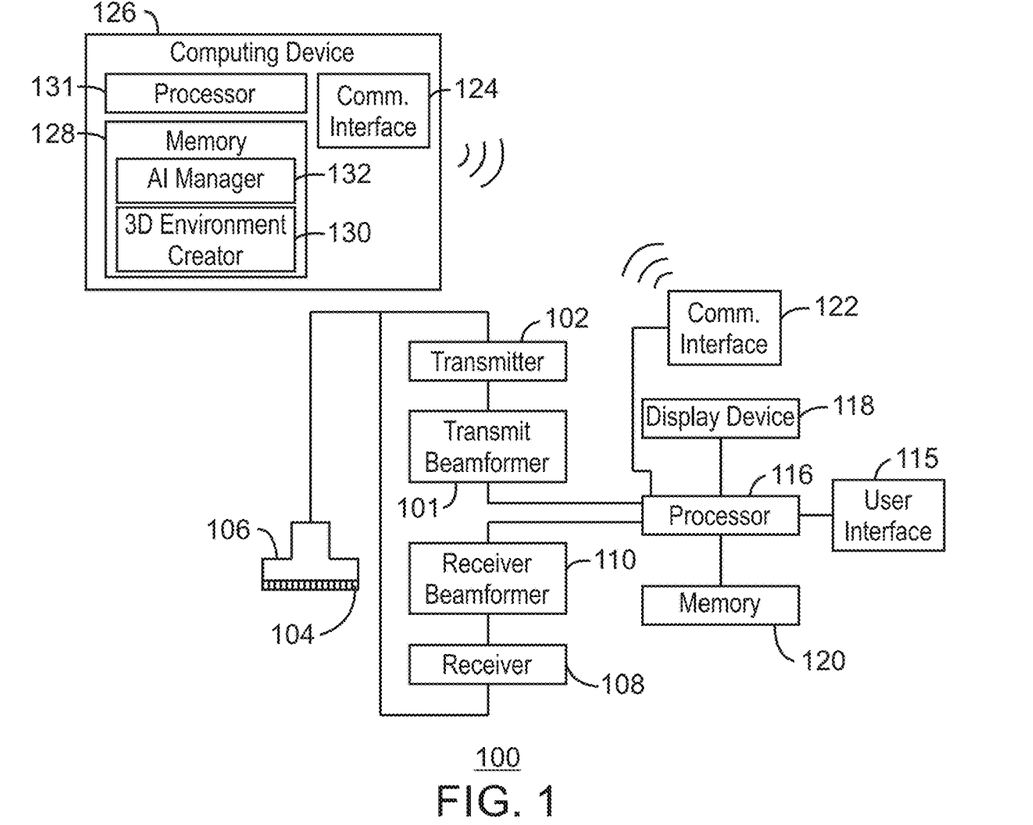
FIG. 1 is a block diagram of an ultrasound imaging system in accordance with an example.

FIG. 1 is a schematic diagram of an ultrasound imaging system 100 in accordance with an example. The ultrasound imaging system 100 includes a transmit beamformer 101 and a transmitter 102 that drive elements 104 within a probe 106 to emit pulsed ultrasonic signals into a body (not shown). The probe 106 may be any type of probe, including a linear probe, a curved array probe, a 1.25D array, a 1.5D array, a 1.75D array, or 2D array probe according to various examples. The probe 106 may also be a mechanical probe, such as a mechanical 4D probe or a hybrid probe according to other examples. The probe 106 may be used to acquire 4D ultrasound data that contains information about how a volume changes over time. Each of the volumes may include a plurality of 2D images or slices. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some examples, the probe 106 may contain electronic circuitry to do all or part of the transmit beamforming and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The terms "data" and "ultrasound data" may be used in this disclosure to refer to either one or more datasets acquired with an ultrasound imaging system. A user interface 115 may be used to control operation of the ultrasound imaging system 100. The user interface 115 may be used to control the input of patient data, or to select various modes, operations, and parameters, and the like. The user interface 115 may include a one or more user input devices such as a keyboard, hard keys, a touch pad, a touch screen, a track ball, rotary controls, sliders, soft keys, or any other user input devices. The user interface is in electronic communication with the processor 116.

The ultrasound imaging system 100 also includes a processor 116 to control the transmit beamformer 101, the transmitter 102, the receiver 108 and the receive beamformer 110. The receive beamformer 110 may be either a conventional hardware beamformer or a software beamformer according to various examples. If the receive beamformer 110 is a software beamformer, it may comprise one or more of the following components: a graphics processing unit (GPU), a microprocessor, a central processing unit (CPU), a digital signal processor (DSP), or any other type of processor capable of performing logical operations. The beamformer 110 may be configured to perform conventional beamforming techniques as well as techniques such as retrospective transmit beamforming (RTB).

The processor 116 is in electronic communication with the ultrasound probe 106, the receiver 108, the receive beamformer 110, the transmit beamformer 101, and the transmitter 102. The processor 116 may control the probe 106 to acquire ultrasound data. The processor 116 controls which of the elements 104 are active and the shape of a beam emitted from the probe 106. The processor 116 is also in electronic communication with a display device 118, and the processor 116 may process the ultrasound data into images for display on the display device 118. For purposes of this disclosure, the term "electronic communication" may be defined to include both wired and wireless connections. The processor 116 may include a central processing unit (CPU) according to an example. According to other examples, the processor 116 may include other electronic components capable of carrying out processing functions, such as a digital signal processor, a field-programmable gate array (FPGA), a graphics processing unit (GPU) or any other type of processor. According to other examples, the processor 116 may include multiple electronic components capable of carrying out processing functions. For example, the processor 116 may include two or more electronic components selected from a list of electronic components including: a central processing unit (CPU), a digital signal processor (DSP), a field-programmable gate array (FPGA), and a graphics processing unit (GPU). According to another example, the processor 116 may also include a complex demodulator (not shown) that demodulates the RF data and generates raw data. In another example the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without enabling additional latency or a delay. Real-time frame or volume rates may vary based on the size of the region or volume from which data is acquired and the specific parameters used during the acquisition. The data may be stored temporarily in a buffer (not shown) during a scanning session and processed in less than real-time in a live or off-line operation. Some examples can include multiple processors (not shown) to handle the processing tasks.

For example, a first processor may be utilized to demodulate and decimate the RF signal while a second processor may be used to further process the data prior to display as an image. It should be appreciated that other examples may use a different arrangement of processors. For examples where the receive beamformer 110 is a software beamformer, the processing functions attributed to the processor 116 and the software beamformer hereinabove may be performed by a single processor such as the receive beamformer 110 or the processor 116. In some examples, the processing functions attributed to the processor 116 and the software beamformer may be allocated in a different manner between any number of separate processing components.

According to an example, the ultrasound imaging system 100 may continuously acquire ultrasound data at a frame-rate of, for example, 10 Hz to 30 Hz. Images generated from the data may be refreshed at a similar frame-rate. Other examples may acquire and display data at different rates. For example, some examples may acquire ultrasound data at a frame rate of less than 10 Hz or greater than 30 Hz depending on the size of the volume and the intended application. For example, many applications involve acquiring ultrasound data at a frame rate of 50 Hz. A memory 120 is included for storing processed frames of acquired data. In an example, the memory 120 is of sufficient capacity to store frames of ultrasound data acquired over a period of time at least several seconds in length. The frames of data are stored in a manner to facilitate retrieval thereof according to its order or time of acquisition. The memory 120 may comprise any known data storage medium.

In some examples, ultrasound data can be acquired, received, or otherwise obtained while utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using any suitable filters.

In various examples, data may be processed by other or different mode-related modules by the processor 116 (e.g., B-mode, color Doppler, M-mode, color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored, and timing information indicating a time at which the data was acquired in memory may be recorded. The modules may include, for example, a scan conversion module to perform scan conversion operations to convert the image frames from beam space coordinates to display space coordinates. A video processor module may be provided that reads the image frames from a memory, such as the memory 120, and displays the image frames in real time while a procedure is being carried out on a patient. A video processor module may store the image frames in an image memory, from which the images are read and displayed.

In some examples, the processor 116 can be electronically coupled to a communication interface 122, which can transmit data to and receive data from a communication interface 124 of a computing device 126. In some examples, the computing device 126 can communicate with the ultrasound imaging system 100 using any suitable protocol such as any wired or wireless data transmission protocol. The computing device 126 can include memory 128 that can store data and applications related to ultrasound imaging techniques described herein. For example, the memory 128 can include a 3D environment creator 130 that can cause a processor 131 to acquire volumes of ultrasound data from the ultrasound imaging system 100 and construct or generate a three-dimensional environment. In some examples, the 3D environment creator 130 can include instructions that create the 3D environment based on volumes of ultrasound data from any number of patients. Generation of a 3D environment is described in greater detail below in relation to FIGS. 4 and 5.

The memory 128 of the computing device 126 can also include an artificial intelligence manager 132 that can include instructions that cause the processor 131 to train, configure, or otherwise initiate a set of artificial intelligence instructions that provide guidance for an ultrasound probe. For example, the artificial intelligence instructions can identify a position, orientation, tilt, or the like, of an ultrasound probe and provide guidance such as a direction, rotation, orientation, or tilt to be applied to the ultrasound probe. The artificial intelligence instructions can provide a sequence of suggested actions or guidance to enable the acquisition of a recommended ultrasound probe path for a predetermined organ or region of a patient. Techniques for generating the artificial intelligence instructions are described below in greater detail in relation to FIGS. 6 and 7.

In some examples, the 3D environment creator 120 and the artificial intelligence manager 132 can be partially, or entirely, implemented in hardware of the ultrasound imaging system 100, the computing device 126, or any combination thereof. For example, the functionality of the 3D environment creator 120 and the artificial intelligence manager 132 can be implemented with an application specific integrated circuit, logic implemented in an embedded controller, or in logic implemented in a processor, among others. In some examples, the functionality of the 3D environment creator 120 and the artificial intelligence manager 132 can be implemented with logic, wherein the logic, as referred to herein, includes any suitable hardware (e.g. a processor, a graphics card, or the like), software (e.g. an application, an operating system, or the like), firmware, or any suitable combination of hardware, software, and firmware.

The various methods and processes, such as the method described below with reference to FIG. 3, can be stored as executable instructions in non-transitory memory on a computing device 126 (or controller) in the ultrasound imaging system 100. In one embodiment, the 3D environment creator 120 and the artificial intelligence manager 132 may include such executable instructions in non-transitory memory, and may apply the methods described herein. In another embodiment, computing device 126 may include the instructions in non-transitory memory, and may apply the methods described herein. In yet another embodiment, the methods and processes described herein may be distributed across the imaging system 100 and the computing device 126.

Figure 2:
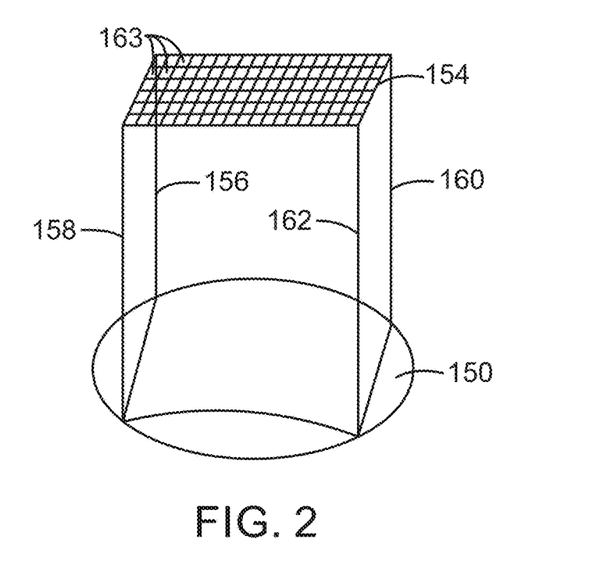
FIG. 2 is a schematic representation for generating a volume-rendered image according to an example.

FIG. 2 is a schematic representation of geometry that may be used to generate a volume-rendering according to an example. FIG. 2 includes a 3D medical imaging dataset 150 and a view plane 154.

Referring to both FIGS. 1 and 2, the processor 116 may generate a volume-rendered image according to a number of different techniques. According to an example, the processor 116 may generate a volume-rendered image through a ray-casting technique, or any other suitable technique, from the view plane 154. For example, the processor 116 can cast or apply a plurality of parallel rays from the view plane 154 to or through the 3D medical imaging dataset 150. FIG. 2 shows a first ray 156, a second ray 158, a third ray 160, and a fourth ray 162 bounding the view plane 154. It should be appreciated that additional rays may be cast in order to assign values to all of the pixels 163 within the view plane 154. The 3D medical imaging dataset 150 may comprise voxel data, where each voxel, or volume-element, is assigned a value or intensity. Additionally, each voxel may be assigned an opacity as well. The value or intensity may be mapped to a color according to some examples. The processor 116 may use a "front-to-back" or a "back-to-front" technique for volume composition in order to assign a value to each pixel in the view plane 154 that is intersected by the ray. For example, starting at the front, that is the direction from which the image is viewed, the intensities of all the voxels along the corresponding ray may be summed. Then, optionally, the intensity can be multiplied by an opacity corresponding to the opacities of the voxels along the ray to generate an opacity-weighted value. These opacity-weighted values are then accumulated in a front-to-back or in a back-to-front direction along each of the rays. The process of accumulating values is repeated for each of the pixels 163 in the view plane 154 in order to generate a volume-rendered image. According to an example, the pixel values from the view plane 154 may be displayed as the volume-rendered image. The rendering algorithm used to generate the volume-rendered image may additionally be configured to use an opacity function providing a gradual transition from opacities of zero (completely transparent) to 1.0 (completely opaque). The rendering algorithm may account for the opacities of the voxels along each of the rays when assigning a value to each of the pixels 163 in the view plane 154. For example, voxels with opacities close to 1.0 will block most of the contributions from voxels further along the ray, while voxels with opacities closer to zero will allow most of the contributions from voxels further along the ray. Additionally, when visualizing a surface, a thresholding operation may be performed where the opacities of voxels are reassigned based on the values. According to an example thresholding operation, the opacities of voxels with values above the threshold may be set to 1.0 while voxels with the opacities of voxels with values below the threshold may be set to zero. Other types of thresholding schemes may also be used. An opacity function may be used to assign opacities other than zero and 1.0 to the voxels with values that are close to the threshold in a transition zone. This transition zone may be used to reduce artifacts that may occur when using a simple binary thresholding algorithm. For example, a linear function mapping opacities to values may be used to assign opacities to voxels with values in the transition zone. Other types of functions that progress from zero to 1.0 may also be used. Volume-rendering techniques other than the ones described above may also be used in order to generate a volume-rendering from a 3D medical imaging dataset.

The volume-rendered image may be shaded and illuminated in order to present the user with a better perception of depth of the rendered object represented in the volume-rendered image. This may be performed in several different ways according to various examples. For example, a surface of a rendered object in the volume-rendered image may be defined based on the volume-rendering of the 3D medical imaging dataset. According to an example, a gradient may be calculated at each of the pixels. The processor 116 (shown in FIG. 1) may compute the amount of light at positions corresponding to each of the pixels and apply standard shading methods based on the gradients and specific light directions. The view direction may correspond with the view direction shown in FIG. 2. The processor 116 may also use multiple virtual light sources as inputs when generating the volume-rendered image. For example, when ray casting, the processor 116 may calculate how much light is reflected, scattered, or transmitted from each voxel in a particular view direction along each ray. This may involve summing contributions from multiple virtual light sources. The processor 116 may calculate the contributions from all the voxels in the volume. The processor 116 may calculate composite values from all of the voxels, or interpolated values from neighboring voxels, in order to compute the final value of the displayed pixel on the image. While the aforementioned example described an implementation where the voxel values are integrated along rays, volume-rendered images may also be calculated according to other techniques such as using the highest value along each ray, using a lowest value along each ray, using an average value along each ray, or using any other volume-rendering technique.

Figure 3:
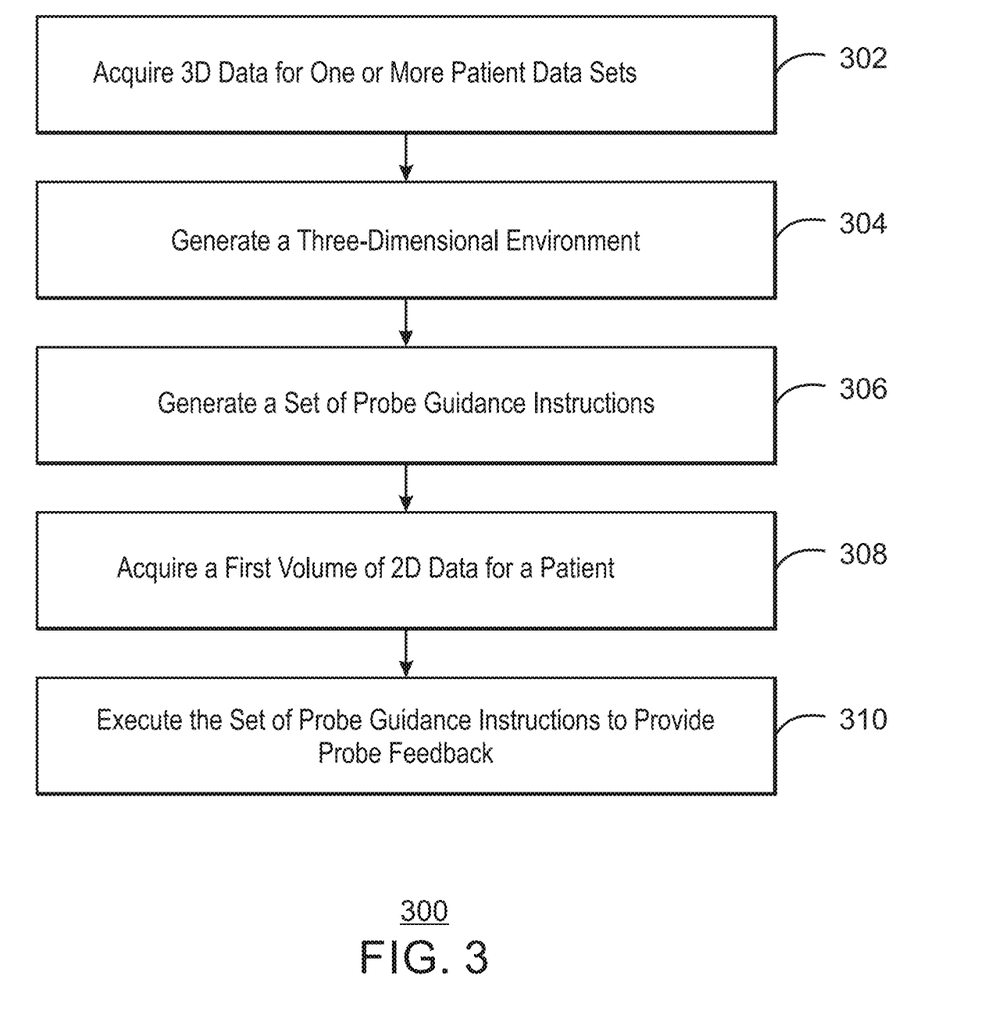
FIG. 3 is a process flow diagram of an example method for generating probe guidance instructions according to an example.

FIG. 3 is a process flow diagram of an example method for generating probe guidance instructions. The method 300 can be implemented with any suitable device. In some examples, the method 300 can be implemented with any suitable device such as the ultrasound imaging system 100 or the computing device 126, among others.

At block 302, the method 300 can include acquiring a three-dimensional image for one or more patient data sets. In some examples, the three-dimensional image can include 3D data such as B-mode, color Doppler, M-mode, color M-mode, spectral Doppler, Elastography, TVI, strain, strain rate, and the like. The three-dimensional data can be acquired, collected, or obtained from any number of patients in the patient data sets. For example, the three-dimensional data can include data from ultrasound probes applied to any number of patients. In some examples, the three-dimensional data can also include any number of volumes per patient. For example, the three-dimensional data can include one or more volumes of data from an abdomen of a patient, one or more volumes from a chest of a patient, and the like. Each volume can represent ultrasound data collected from a region of a patient. In some examples, as the ultrasound is rotated, reoriented, or moved, the ultrasound probe can obtain subsequent volumes.

In some examples, the three-dimensional data corresponds to one or more internal body structures, such as blood vessels, tendons, joints, muscles, and organs, among others, specified by a protocol. The protocol can include a starting point or position to acquire the three-dimensional data, an end point to stop acquiring the three-dimensional data, and the like. In some examples, the three-dimensional data can represent a fetus, a gallbladder, a liver, a kidney, lungs, a heart, or a brain, among others.

At block 304, the method 300 can include generating a three-dimensional environment based on one or more transition areas identified between a plurality of volumes of the three-dimensional data. Each transition area, as referred to herein, can indicate a boundary area between two volumes of data, a non-boundary area adjacent to a boundary area between two volumes, or a combination thereof. For example, each transition area can indicate a boundary between sets of data collected or obtained from an ultrasound probe. Each volume can represent a predetermined range of data acquired with an ultrasound probe. For example, a volume can represent data from any suitable range or area of a region of interest acquired by an ultrasound probe. The volumes can be acquired along a sagittal scanning plane, a transverse scanning plane, or a coronal scanning plane, among others. The transition area can represent a boundary between volumes or acquisitions in any suitable direction such as an anterior direction, a posterior direction, a lateral direction, a medial direction, a superior direction, or an inferior direction, among others. In some examples, any number of volumes for a patient can be normalized within the patient data set. For example, volumes obtained from a patient can be normalized by matching image intensities in regions where volumes overlap. Normalization of volumes can also be performed using any suitable techniques described below in relation to FIG. 5.

In some examples, the three-dimensional environment can be generated or determined based on freehand data collection with an ultrasound probe, which involves tilting the ultrasound probe and capturing a series of ultrasound images and recording the transducer orientation for each slice. The three-dimensional environment can also be acquired mechanically, where the internal linear array is tilted, managed, or controlled by a motor inside the ultrasound probe. For example, the internal linear ultrasound probe tilt can sweep in any suitable direction to acquire three-dimensional ultrasound data. In some examples, the three-dimensional environment is generated using a matrix array transducer that uses beamsteering to sample points throughout a pyramid shaped volume.

The volumes can be combined or stitched together using any suitable technique based on intensity, segmentation, or landmark points, among others, described in greater detail below in relation to FIGS. 4 and 5.

At block 306, the method 300 can include generating a set of probe guidance instructions based at least in part on the one or more transition areas and the plurality of volumes of the three-dimensional data. In some examples, the probe guidance instructions can indicate if an ultrasound probe is to be moved in a particular direction, such as left, right, or center, for a subsequent volume of two-dimensional data to be obtained or acquired. The set of probe guidance instructions can indicate a predetermined path for an ultrasound probe to move within a protocol. For example, the set of probe guidance instructions can indicate a direction, scan angle, position, and the like, for acquiring ultrasound imaging data for a particular protocol or scan of an organ. Once the set of probe guidance instructions are generated, the ultrasound probe is initialized and can be utilized in real-time with a patient.

In some examples, the method 300 can include generating the set of probe guidance instructions using any suitable artificial intelligence technique. For example, reinforcement learning can be used to initialize or calibrate a cost function that indicates a recommended path for the ultrasound probe to follow while acquiring two-dimensional data. In some examples, the reinforcement learning technique can separate each volume of the three-dimensional environment into a set of two-dimensional slices. Based on a beginning two-dimensional slice, the reinforcement learning technique can then identify a subsequent two-dimensional slice from a subsequent volume of the three-dimensional environment that does not include artifacts or other objects that obscure data to be acquired for an internal body structure. The reinforcement learning technique can return a penalty for two-dimensional slices that have artifacts or a reward for two-dimensional slices that do not have an artifact. The initialized reinforcement learning technique can indicate in real-time a subsequent volume of data to be acquired from an ultrasound probe and return instructions for moving the ultrasound probe to collect the subsequent volume as described in greater detail below.

At block 308, the method 300 can include acquiring, using an ultrasound probe, a first frame of two-dimensional data for a patient. For example, the method 300 can include detecting a patient is to be scanned with an ultrasound probe based on a predetermined protocol. As discussed above, the protocol can indicate a starting point for the ultrasound probe, and an end point for the ultrasound probe, among other information. The ultrasound probe can travel any suitable distance to acquire the first frame of two-dimensional data for the patient. The first frame can include imaging data representing a portion of any suitable organ or any other region of interest a patient.

At block 310, the method 300 can include executing the set of probe guidance instructions to provide probe feedback for acquiring at least a second volume of two-dimensional data. In some examples, the probe feedback can provide guidance to a user controlling an ultrasound probe to enable the user to capture or acquire an expected scan plane of one or more organs or other internal body structures of a protocol. The expected scan plane can exclude artifacts and can ensure the ultrasound two-dimensional data is acquired from the patient at an expected angle, position, and the like. In some examples, the probe guidance instructions can include a sequence of actions for the ultrasound probe to follow to acquire the expected scan plane. For example, the probe guidance instructions can include a different direction, rotation, orientation, tilt, or the like for each subsequent volume to be acquired until an end point for acquiring ultrasound data is reached. In some examples, the probe guidance instructions can indicate a movement to be applied to an ultrasound probe to enable the acquisition of a subsequent volume of two-dimensional data along an expected anatomical scanning plane.

In some examples, the probe guidance instructions can be provided via text displayed on a display device within an ultrasound probe or connected to the ultrasound probe. The probe guidance instructions can also be provided using any number of directional arrows displayed by a display device, any audio sounds or video indicating a subsequent recommended path of an ultrasound probe, or the like.

The process flow diagram of method 300 of FIG. 3 is not intended to indicate that all of the operations of blocks 302-310 of the method 300 are to be included in every example. Additionally, the process flow diagram of method 300 of FIG. 3 describes a possible order of executing operations. However, it is to be understood that the operations of the method 300 can be implemented in various orders or sequences. In addition, in some examples, the method 300 can also include fewer or additional operations.

FIG. 4 is a schematic diagram of an example set of volumes used to create a three-dimensional environment. The three-dimensional environment 400 can be created using any suitable combination of software and hardware, such as the 3D environment creator 120 implemented by the ultrasound imaging system 100 or the computing device 126 of FIG. 1, among others.

In some examples, any number of volumes 402, 404, 406, and 408 can be acquired, received, or otherwise obtained. The volumes 402, 404, 406, and 408 can represent regions of interest of a patient in three-dimensional space such that the volumes 402, 404, 406, and 408 can share boundaries along an x-axis, a y-axis, a z-axis, or a combination thereof. For example, the illustration in FIG. 4 provides an example of volumes 402, 404, 406, and 408 sharing boundaries along the x-axis and y-axis. In some examples, the volumes 402, 404, 406, and 408 can also share any number of boundaries along a z-axis.

In some examples, boundaries between the volumes are determined based on a change in the elevation, azimuth, or any other suitable data for an ultrasound probe. Any number of volumes 402, 404, 406, and 408 can be combined in three-dimensional cartesian space, such as along an x-axis, a y-axis, and a z-axis. For example, volumes 402, 404, 406, and 408 can be combined to form the three-dimensional environment with transition areas based on a depth of acquired volumes, a width of acquired volumes, or a length of the acquired volumes along a scan plane of an ultrasound probe. In some examples, a transition function can define transition areas or boundaries between any number of volumes of ultrasound data. For example, the transition function can be defined as $V=T(A_t, A_{t+1}, V_i)$, in which A represents an action, such as a change in direction, rotation, orientation, or tilt, of an ultrasound probe and t represents a current time or position of the ultrasound probe, while Vi represents a current volume of ultrasound data.

FIG. 5 shows example techniques for determining a transition area between volumes. The technique 500 can be implemented with any suitable computing device such as the ultrasound imaging system 100 or the computing device 126 of FIG. 1, among others.

In some examples, two or more volumes 502A and 504A of three-dimensional data acquired from an ultrasound probe can be joined to form a three-dimensional environment based on an intensity of the data of the two or more volumes 502A and 504A. For example, a difference operation can be applied to the data representing two adjacent volumes and a lowest or a minimum value calculated by the difference operation can indicate a transition area between the two volumes. In some examples, the difference operation is applied to the data of the two adjacent volumes to simulate rotating the volumes around any suitable axis, such as an x-axis, a y-axis, or a z-axis. A lowest difference calculated with the two volumes can represent a transition area or boundary between two volumes and an expected orientation of the two volumes with respect to one another.

In some examples, two or more volumes 502B and 504B of three-dimensional data acquired from an ultrasound probe can be joined to form a three-dimensional environment based on segmentation shared between the two or more volumes 502B and 504B. For example, a difference between segmentation maps of two adjacent volumes can be used to identify the rotation or translation, among others. The difference can be calculated using any suitable difference operation based on segmentation of tissue in a volume according to density or any other characterization.

In some examples, two or more volumes 502C and 504C of three-dimensional data acquired from an ultrasound probe can be joined to form a three-dimensional environment based on landmark points identified within the two or more volumes 502C and 504C. The landmark points can indicate identified points within any number of organs, muscles, joints, or other areas of interest of a patient. For example, a distance metric, such as a Euclidian distance, among others, between corresponding landmark points can be measured and the geometric transformation minimizing the distance metric can be considered as the expected orientation or alignment of the two adjacent volumes.

FIG. 6 is a block diagram of an example block diagram for generating the probe guidance instructions. The block diagram 600 can be implemented with any suitable computing device such as the ultrasound imaging system 100 or the computing device 126 of FIG. 1, among others.

In some examples, a three-dimensional environment 602 can be used to train an agent 604. The agent 604 can be any suitable set of artificial intelligence instructions that can identify a path for an ultrasound probe to follow to acquire two-dimensional data of one or more organs or any other suitable internal body structures identified by a protocol. In some examples, the agent 604 can access, generate, or otherwise detect 606 two-dimensional data or slices from the three-dimensional environment 602. In some examples, two-dimensional data or data slices that do not represent two-dimensional slices of data that can be acquired with a two-dimensional ultrasound probe may be excluded. A state of the ultrasound probe and an action can be simulated 608 using the two-dimensional slices to identify or determine the path that an ultrasound probe is to follow to prevent the acquisition of artifacts in the two-dimensional data. The action can include a change in an orientation of the ultrasound probe, a tilt of the ultrasound probe, or a change in a position of the ultrasound probe in three-dimensional space, among others.

The simulated action and the state of the simulated ultrasound probe can be provided 610 to any suitable artificial intelligence software or model to identify a recommended set of actions for the ultrasound probe to use while acquiring two-dimensional data. In some examples, the artificial intelligence software or model can use a neural network, a random forest model, deep learning techniques, or reinforcement learning techniques, among others. For example, the artificial intelligence software can initialize a cost function and optimize 612 the cost function based on rewards and penalties identified as the simulated ultrasound probe acquires data from the two-dimensional slices of the three-dimensional environment. In some examples, a reward of any number of points can be assigned to two-dimensional slices of data obtained from a subsequent volume of a three-dimensional environment without artifacts, blurry regions, or the like. The reward can also assign any number of points to the selection of the expected subsequent volume from the three-dimensional environment, a second simulated frame, or the subsequent two-dimensional image acquired from a volume of a previous two-dimensional image. In some examples, the penalty can be any number of points that represent an unexpected volume selected from the three-dimensional environment or the selection of a two-dimensional slice from a volume of the three-dimensional environment that includes one or more artifacts, blurry regions, obstructions, and the like. In some examples, the reward and penalty can be based on producing a simulated two-dimensional image from a three-dimensional environment, wherein the two-dimensional image is along an expected anatomical scanning plane.

In some examples, the cost function is initialized for each organ or region of a patient so that a first cost function represents a recommended path of an ultrasound probe to acquire two-dimensional data of a kidney and a second cost function represents a recommended path of an ultrasound probe to acquire two-dimensional data of lungs, or any other suitable organs. Any number of cost functions can be generated and initialized for any number of organs. In some examples, a single cost function can be generated and initialized based on an ultrasound probe acquiring three-dimensional data for multiple organs such as a kidney and liver, or any other organs or regions of a patient.

In some examples, the next action 614 is the output of the reinforcement learning, which can be combined as a sequence of recommended actions for an ultrasound probe to use while acquiring two-dimensional data. The reinforcement learning can stop generating output when there are no additional two-dimensional slices to acquire from the three-dimensional representation or when the cost function results in an accuracy above a predetermined threshold. In some examples, the reinforcement learning can also stop or terminate after a predetermined number of iterations or based on validation data that indicates an expected accuracy of the reinforcement learning model.

FIG. 7 is a process flow diagram for generating probe guidance instructions used to acquire three-dimensional data. The method 700 can be implemented with any suitable computing device such as the ultrasound imaging system 100 or the computing device 126 of FIG. 1, among others.

In some examples, the generated three-dimensional environment described above in relation to FIGS. 3-5 can be used as a simulated environment to generate probe guidance instructions. For example, the three-dimensional environment can be sliced or separated into any number of two-dimensional sets of data that can be navigated in a simulated environment. In some examples, at block 702, the method 700 includes detecting, receiving, or otherwise obtaining an ultrasound probe state and an action. The ultrasound probe state can indicate a location, angle, tilt, rotation, and the like of a simulated ultrasound device acquiring data from the generated three-dimensional environment. For example, the probe state can indicate a two-dimensional slice of data obtained from the three-dimensional environment. In some examples, the action can represent a simulated action used to acquire the two-dimensional slice of data. For example, the action can represent any suitable simulated movement of a simulated ultrasound probe to select data, such as the two-dimensional slice, from the generated three-dimensional environment.

In some examples, at block 704, the method 700 can include determining a subsequent volume to acquire and an action to be applied to the ultrasound probe to acquire the subsequent volume. For example, a cost function can provide guidance to determine a next volume of data to be acquired from the generated three-dimensional environment.

At block 706, the method 700 can include obtaining or selecting or acquiring a simulated frame from the three-dimensional environment, such as a two-dimensional slice of data from the next selected volume of data 705 from the generated three-dimensional environment. In some examples, the two-dimensional slice of data is selected or obtained by applying an action identified with the probe guidance instructions. For example, reinforcement learning techniques described above in relation to FIG. 6 can be used to identify a simulated action for the ultrasound probe to use to change an orientation, position, direction, rotation, tilt, or the like, for acquiring the next two-dimensional slice of data.

At block 708, the method 700 can include imposing a scan cone mask to the simulated frame or two-dimensional slice to represent the output from an ultrasound probe used in real-time while acquiring three-dimensional data from a patient. The scan cone mask can disregard, mask, block, delete, or otherwise remove portions of the simulated two-dimensional data slice obtained from the three-dimensional environment. For example, the scan cone mask can remove or mask portions of the two-dimensional slice that would not be captured or acquired with an ultrasound probe. The scan cone mask can result in a portion of the two-dimensional slice that matches a cone shaped segment of data acquired by an ultrasound probe.

At block 710, the method 700 can include augmenting the simulated frame or image based on non-geometric configuration settings of an ultrasound probe such as a gain, intensity, and the like. In some examples, the non-geometric configuration settings can include any settings provided by an ultrasound probe. The result of the image augmentation is a simulated two-dimensional representation of the output that an ultrasound probe can provide during a real-time diagnostic scan of a patient.

The process flow diagram of method 700 of FIG. 7 is not intended to indicate that all of the operations of blocks 702-710 of the method 700 are to be included in every example. Additionally, the process flow diagram of method 700 of FIG. 7 describes a possible order of executing operations. However, it is to be understood that the operations of the method 700 can be implemented in various orders or sequences. In addition, in some examples, the method 700 can also include fewer or additional operations.

FIG. 8 is a non-transitory machine-executable medium for identifying a recommended path for an ultrasound probe. The non-transitory, machine-readable medium 900 can implement the functionalities of the ultrasound imaging system 100 of FIG. 1, the computing device 126 of FIG. 1, or a combination thereof, among others. For example, a processor 802 in an ultrasound imaging system 100, a computing device 126, or any other suitable device, can access the non-transitory, machine-readable media 800.

In some examples, the non-transitory, machine-readable medium 800 can include instructions to execute a 3D environment creator 120, an artificial intelligence manager 132, or a combination thereof. For example, the non-transitory, machine-readable medium 900 can include instructions for the 3D environment creator 120 and the artificial intelligence manager 132 that cause the processor 902 to generate a three-dimensional representation of volumes of ultrasound data and to generate probe guidance instructions to provide a recommended path for acquiring ultrasound data. The non-transitory, machine-readable medium 900 can also include instructions to implement any combination of the features of the 3D environment creator 120 and the artificial intelligence manager 132 described in examples above.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A method for ultrasound imaging comprising:
acquiring three-dimensional data for one or more patient data sets;
generating a three-dimensional environment based on one or more transition areas identified between a plurality of volumes of the three-dimensional data, wherein the one or more transition areas are determined based at least in part on a plurality of intensity values representing the three-dimensional data;
generating a set of probe guidance instructions based at least in part on the three-dimensional environment, wherein the set of probe guidance instructions indicate an expected scan plane that excludes an artifact, wherein the generating the set of probe guidance instructions comprises determining a cost function using a machine learning technique based at least on a simulated frame acquired from the three-dimensional environment, wherein the cost function is initialized based on at least two organs to be scanned from a region of the one or more patient data sets;
acquiring, using an ultrasound probe, a first frame of two-dimensional data for a patient; and
executing the set of probe guidance instructions to provide probe feedback for acquiring at least a second frame of two-dimensional data for the patient.

2. The method of claim 1, wherein the probe feedback comprises a recommended ultrasound probe path for the ultrasound probe.

3. The method of claim 2, wherein the recommended ultrasound probe path of the ultrasound probe comprises a direction of the ultrasound probe, a subsequent scan angle of the ultrasound probe, or a combination thereof.

4. The method of claim 2 further comprising displaying the recommended ultrasound probe path using a display device electronically coupled to the ultrasound probe.

5. The method of claim 2, further comprising displaying, using a user interface, a real-time image and displaying the recommended ultrasound probe path with the user interface.

6. The method of claim 1, wherein the ultrasound probe comprises a three-dimensional ultrasound probe or a two-dimensional ultrasound probe.

7. The method of claim 1, wherein at least one three-dimensional ultrasound probe acquires the three-dimensional data for the one or more patient data sets, and wherein the ultrasound probe that acquires the first frame is a two-dimensional ultrasound probe that acquires the two-dimensional data that is used to execute the set of probe guidance instructions.

8. The method of claim 1, further comprising imposing a scan cone mask to the simulated frame to represent output from the ultrasound probe.

9. The method of claim 8, further comprising augmenting the simulated frame based on non-geometric configuration settings of the ultrasound probe.

10. The method of claim 1, wherein each volume of the three-dimensional data comprises Doppler data from one or more regions of a patient, B-mode data from the one or more regions of the patient, or a combination thereof.

11. An ultrasound imaging system comprising:
a display device to provide a user interface;
an ultrasound probe; and
a processor to:
- acquire three-dimensional data for one or more patient data sets;
- generate a three-dimensional environment based on one or more transition areas identified between a plurality of volumes of the three-dimensional data, wherein the one or more transition areas are determined based at least in part on a plurality of intensity values representing the three-dimensional data;
- generate a set of probe guidance instructions based at least in part on the one or more transition areas and the plurality of volumes of the three-dimensional data, wherein the set of probe guidance instructions indicate an expected scan plane that excludes an artifact, wherein the generating the set of probe guidance instructions comprises determining a cost function using a machine learning technique based at least on a simulated frame acquired from the three-dimensional environment, wherein the cost function is initialized based on at least two organs to be scanned from a region of the one or more patient data sets;
- acquire, using the ultrasound probe, a first frame of two-dimensional data for a patient;
- execute the set of probe guidance instructions to provide probe feedback for controlling the ultrasound probe to acquire at least a second frame of two-dimensional data; and
- display the probe feedback using the display device.

12. The ultrasound imaging system of claim 11, wherein the probe feedback comprises a recommended ultrasound probe path for the ultrasound probe.

13. The ultrasound imaging system of claim 11, wherein the ultrasound probe comprises a three-dimensional ultrasound probe or a two-dimensional ultrasound probe.

14. The ultrasound imaging system of claim 11, wherein a second three-dimensional ultrasound probe acquires the three-dimensional data for the one or more patient data sets, and wherein the ultrasound probe that acquires the first frame is a two-dimensional ultrasound probe that executes the set of probe guidance instructions.

15. The ultrasound imaging system of claim 11 further comprising displaying a recommended ultrasound probe path using the display device electronically coupled to the ultrasound probe.

16. A non-transitory machine-readable medium for ultrasound imaging comprising a plurality of instructions that, in response to execution by a processor, cause the processor to:
- acquire three-dimensional data for one or more patient data sets;
- generate a three-dimensional environment based on one or more transition areas identified between a plurality of volumes of the three-dimensional data, wherein the one or more transition areas are determined based at least in part on a plurality of intensity values representing the three-dimensional data and at least one opacity-weighted value;
- generate a set of probe guidance instructions based at least in part on the one or more transition areas and the plurality of volumes of the three-dimensional data, wherein the set of probe guidance instructions indicate an expected scan plane that excludes an artifact, wherein the generating the set of probe guidance instructions comprises determining a cost function using a machine learning technique based at least on one or more simulated frames acquired from the three-dimensional environment, wherein the cost function is initialized based on at least two organs to be scanned from a region of the one or more patient data sets;
- acquire, using an ultrasound probe, a first frame of two-dimensional data for a patient;
- execute the set of probe guidance instructions to provide probe feedback for controlling the ultrasound probe to acquire at least a second frame of two-dimensional data; and
- display the probe feedback using the display device, wherein the probe feedback comprises a recommended ultrasound probe path of the ultrasound probe comprising a direction of the ultrasound probe, a subsequent scan angle of the ultrasound probe, or a combination thereof.

17. The non-transitory machine-readable medium of claim 16, wherein the at least one opacity-weighted value is generated with one or more of the plurality of intensity values combined with at least one opacity value.

* * * * *